US00PP13195P2

(12) United States Plant Patent
Utecht

(10) Patent No.: US PP13,195 P2
(45) Date of Patent: Nov. 5, 2002

(54) GERANIUM PLANT NAMED 'FISBLUFORT'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/989,135

(22) Filed: Nov. 21, 2001

(65) Prior Publication Data

US 2002/0083500 P1 Jun. 27, 2002

(51) Int. Cl.[7] ..... A01H 5/00

(52) U.S. Cl. ..... Plt./329

(58) Field of Search ..... Plt./329, 325

*Primary Examiner*—Kent L. Bell
(74) *Attorney, Agent, or Firm*—Foley & Lardner

(57) ABSTRACT

A new and distinct cultivar of geranium plant named 'Fisblufort', as described and illustrated, and particularly characterized by the combined features of large, bright pink flowers with rose eyes, medium-green foliage with slight zonation, medium sized, round plant habit, and early to medium spring flowering response.

1 Drawing Sheet

BOTANICAL CLASSIFICATION

*Pelargonium zonale.*

VARIETY DENOMINATION

'Fisblufort'.

BACKGROUND OF THE INVENTION

The present invention comprises a new and distinct cultivar of geranium, botanically known as *Pelargonium zonale*, and hereinafter referred to by the cultivar name 'Fisblufort'.

'Fisblufort' is a product of a planned breeding program which had the objective of creating new geranium varieties with pink flowers with eyes on petals in combination with deep green foliage, and well-branched, round plant habit.

'Fisblufort' originated from a hybridization made by the inventor Angelika Utecht in a controlled breeding program in Galdar, Gran Canaria, Spain, in 1996. The female parent was the patented cultivar 'Fisbravo' (U.S. Plant Pat. No. 9,765), which is characterized by pink colored flowers with large purple eyes, dark-green, slightly zoned foliage and moderately compact plant habit. The male parent of 'Fisblufort' was the variety 'Blues', having pink flower color with rose-red flares, deep green foliage without zonation, and medium sized, low spreading plant habit.

'Fisblufort' was selected as one flowering plant within the progeny of the stated cross by Angelika Utecht in 1997, in a controlled environment in Galdar, Gran Canaria, Spain.

The first act of asexual reproduction of 'Fisblufort' was accomplished when vegetative cuttings were taken from the initial selection in the fall of 1997 in a controlled environment in Galdar, Gran Canaria, Spain, by, or under the supervision of, Angelika Utecht.

Horticultural examination of plants grown from cuttings of the plant initiated in May 1998, in Hillscheid, Federal Republic of Germany, and continuing thereafter, has demonstrated that the combination of characteristics as herein disclosed for 'Fisblufort' are firmly fixed and are retained through successive generations of asexual reproduction. The new cultivar reproduces true to type.

'Fisblufort' has not been observed under all possible environmental conditions. The phenotype may vary significantly with variations in environment such as temperature, light intensity and day length. The following observations, measurements, and comparisons describe plants grown in Hillscheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fisblufort' in combination distinguish this geranium as a new and distinct cultivar:

1. Bright pink, semi-double flowers with rose-red and white markings;
2. Floriferous with medium sized, semi-spherically shaped inflorescence;
3. Medium green foliage with slight zonation;
4. Medium vigor, and tight, rounded plant habit; and
5. Early to medium spring flowering response.

Of the many commercial cultivars known to the present inventor, the most similar in comparison to 'Fisblufort' are the patented varieties 'Blues' (U.S. Plant Pat. No. 5,373), and 'Fisblu' (U.S. Plant Pat. No. 9,764).

In comparison to 'Blues', 'Fisblufort' has an almost similar main general flower color, with the reddish eyes on petals somewhat more distinct, foliage with somewhat stronger zonation, and somewhat more vigorous, better branched, and more upright growth.

In comparison to 'Fisblu', 'Fisblufort' has a somewhat lighter flower color with less deep red markings on petals, larger foliage with weak zonation ('Fisblu' has no zonation) and distinctly taller plant habit.

BRIEF DESCRIPTION OF THE DRAWING

The accompanying photographic drawing shows typical flower and foliage characteristics of 'Fisblufort' with colors being as true as possible with an illustration of this type. The drawings shows a flowering pot plant in a 14 cm container.

DETAILED BOTANICAL DESCRIPTION

In the following description color references are made to The Royal Horticultural Society Colour Chart. The color values were determined indoors from plants developed in a green-house in May 2001, in Hillscheid, Germany. The measurements were taken in Hillscheid, Germany in mid May 2001, 10 weeks after planting of rooted cuttings. The plants were growing in 14 cm inch containers and had not been pinched.

Inflorescence:
- *Type.*—Umbel.
- *Shape.*—Semi-spherical.
- *Average diameter.*—104 mm.
- *Average depth.*—60 mm.
- *Peduncle length.*—134 mm.
- *Peduncle color.*—Light green, RHS 144 A.
- *Pedicel, length.*—29 mm.
- *Pedicel color.*—Mainly grass green, RHS 143 A, upper end brown, RHS 179 A.
- *Number of flowers per umbel.*—About 25–35.

Corolla:
- *Average diameter.*—49.5 mm.
- *Form.*—Semi-double.
- *Shape.*—Round, cup-shaped, appearance almost like single-type flowers.
- *Number of petals.*—6.3.
- *Number of petaloids.*—0–1, narrow, same color as the petals.
- *Shape of petals.*—Obovate, base attenuate, upper end is rounded or with very slight serrulation at the apex, margin is entire.
- *Size of petals.*—Upper petals 24–26 mm long, 21–24 mm wide; lower petals 22–24 mm long, 23–25 mm wide.
- *Color (general tonality from a distance of three meters).*—Bright pink with rose and white markings.
- *Color of upper petals.*—Main part RHS 68 B.
- *Markings of upper petals.*—Rose eye, RHS 57 C, about 7–8 mm in diameter, and white base, RHS 155 D, covering the lower third part, fine veins, RHS 74 B.
- *Color of lower petals.*—Near RHS 61 D.
- *Markings of lower petals.*—Small eye, RHS 52 A, about 3–5 mm in diameter, and very light pink base, RHS 68 D.
- *Color of lower surface of petals.*—Light pink, RHS 68 C to RHS 68 D.
- *Color of sepals.*—Outer surface light green, RHS 144 A; inner surface light green, RHS 144 B.
- *Number of sepals.*—5.
- *Shape of sepals.*—Linear to lanceolate, acute tip, truncate base, surface with very short pubescence, margin entire.
- *Size of sepals.*—11–12 mm long, 4 mm wide for the largest upper sepal, 2–3 mm in width for the other sepals.

Bud: (just before petals unfold):
- *Shape.*—Narrow elliptical.
- *Color (sepals).*—Light green, RHS 144 A.
- *Color (petals).*—Light pink, RHS 73 B.
- *Length.*—20 mm.
- *Width.*—10 mm.

Reproductive organs:
- *Androecium.*—7 fertile anthers, white filaments, plenty pollen, orange, RHS 30 A.
- *Gynoecium.*—One pistil, style and stigma pink, RHS 51 A, 5 to 6 lobed stigma.
- *Fertility/seed set.*—Occasionally a few feeds are developed. Fruit: Oblong, about 5–6 mm in diameter, with rostrum (beak), total length 40 mm. Seed: Oblong, 4–5 mm long, brown, RHS 177 B.

Spring flowering response period: In Hillscheid, Germany, in 2000 plants had on average 1.4 flowers opened 8 weeks after planting of rooted cuttings.

Outdoor flower production: Continuously flowering, the flower count in 2000 in Hillscheid, Germany, indicated about 3.0 inflorescence per plant in mid May.

Durability: Good stability of flower color, good rain resistance, good heat tolerance.

Lastingness of the individual flower: About 8 days at 18° C., about 20 days for the umbel.

Pest/disease resistance/susceptibility: No observations to date.

Fragrance: None.

PLANT

Foliage:
- *Shape.*—Kidney-shaped, with open, cordate base, weak lobes.
- *Margin.*—Bicrenated.
- *Texture.*—Upper surface smooth, velvety.
- *Size of leaf.*—97 mm wide, 57 mm long.
- *Color of upper surface.*—Medium green, approximately RHS 137 C.
- *Color of zonation.*—Dark green, about RHS 147 A, may not always be visible on mature leaves during the summer.
- *Petioles.*—50–60 mm long, 3 mm diameter, light green in color, approximately RHS 143 B.

General appearance and form:
- *Stem color.*—Green, RHS 143 A.
- *Internode length.*—10–15 mm.
- *Branching pattern.*—6.0 branches.
- *Size of plants.*—Height 14.9 cm, as measured from the top of the soil (base of the main stem) to the surface of the foliage canopy, measured without inflorescences; width 28.5 cm.

I claim:

1. A new and distinct cultivar of geranium plant named 'Fisblufort', as described and illustrated herein.

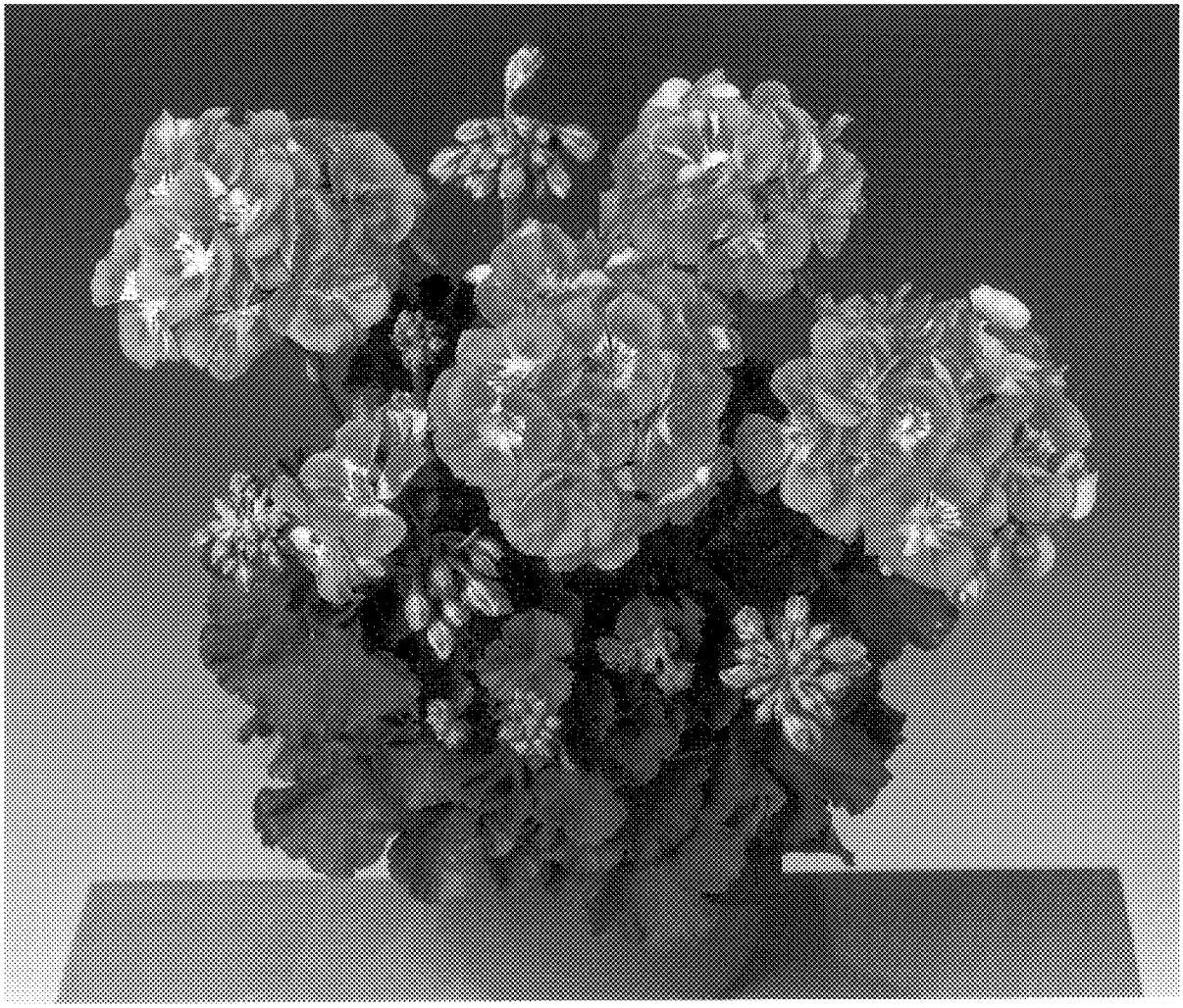

* * * * *